Aug 6, 1974 G. MERRILL Plant Pat. 3,582
PEACH
Filed March 30, 1972
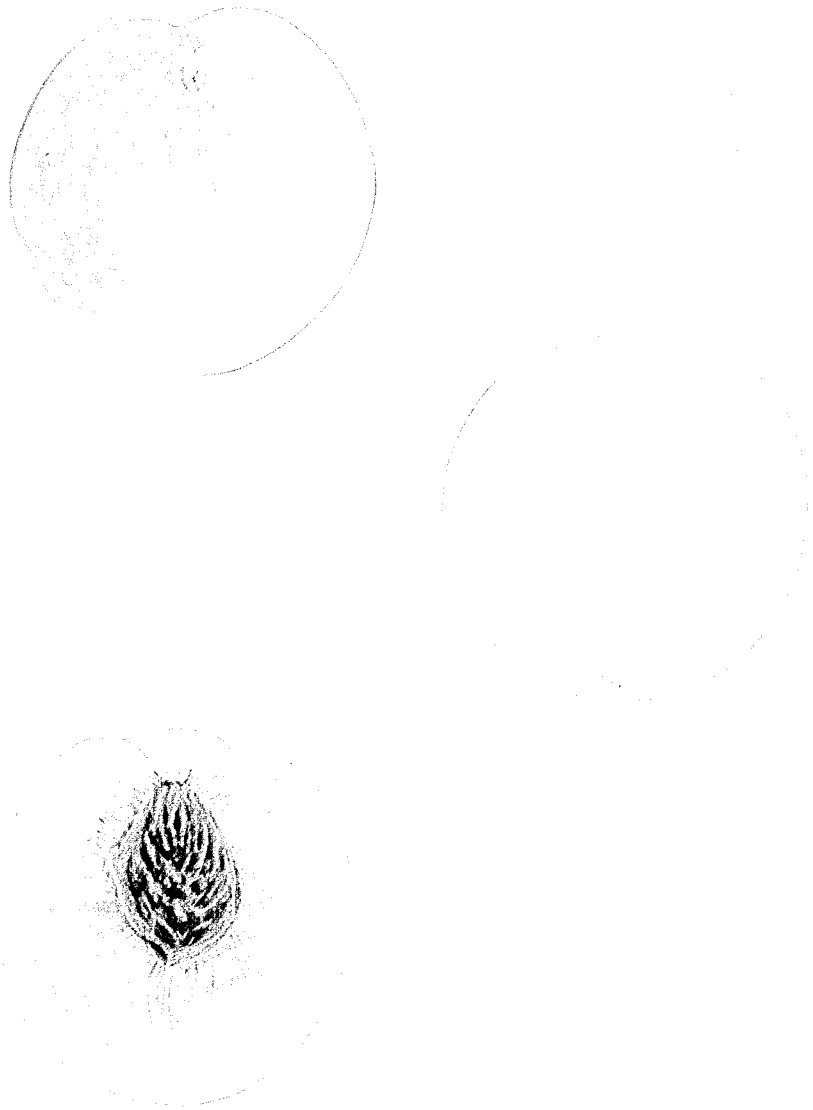

United States Patent Office

Plant Pat. 3,582
Patented Aug. 6, 1974

3,582
PEACH TREE

Grant Merrill, 416 N. Anderson Road,
Exeter, Calif. 93221

Filed Mar. 30, 1972, Ser. No. 239,829
Int. Cl. A01h *5/03*
U.S. Cl. Plt.—43 1 Claim

The present invention relates to a peach tree and more particularly to a new and distinct variety thereof broadly characterized by a moderately vigorous tree, regularly bearing fruit which is large and firm and has a red blush and stripe covering one-fourth to three-fourths of its surface, depending on exposure to sun, age of tree, pruning, fertilizing and watering, and a bright yellow undercolor. It is further characterized by having a longer than usual stem, thus reducing the amount of stem crease in large fruit, and by the stem clinging tightly to the fruit and to the twig and thereby resulting in almost no dropping of fruit as it matures. The fruit ripens in late September to early October in Fresno and Tulare counties in California.

The instant variety of peach most nearly resembles Merrill Halloween I (U.S. P.P. 1,473), ripening about the same time but distinguishable therefrom and an improvement thereon by its redder skin color, its longer stem which clings more tightly to the fruit and the twig and results in much less natural drop as the fruit matures (as is common with Halloween I), and by a less vigorous tree which enables it to be planted closer and grown lower so a shorter ladder and less effort is required to prune, thin, and pick the fruit.

I originated the present variety of peach (my identification number 36–86A) on a farm formerly owned by me at Red Bluff, Tehama County, Calif., as follows. I hand crossed, without bagging, Fiesta (U.S. P.P. 1,099) with a late ripening peach of unknown parentage found growing in my experimental plot. A seedling thus produced, the instant variety, was then asexually reproduced by budding onto a small tree which I then transplanted to my farm at Exeter, Tulare County, Calif. The fruit and tree characteristics remained the same as those of the original fruit and tree (seedling 36–86A) and worthy of commercial use.

The accompanying drawing is an oil painting of a characteristic mature fruit of the subject variety showing the shape and skin color, and by means of a fruit divided on its suture plane, showing the flesh and stone color and the freedom of the flesh from the stone in a mature fruit.

Referring now more specifically to the pomological characteristics of this new and distinct variety of peach tree, the following is an outline description thereof observed under the ecological conditions prevailing in Tulare County, Calif. All major color plate identifications are by reference to Maerz and Paul's Dictionary of Color, First Edition.

TREE

Size: medium size, vigor and density; may be pruned to vase shape.
Trunk: straight, medium stocky, shaggy and gray.
Branches: older branches gray, brown when young; straight with some bending.
Lenticels: medium in size and quantity.
Twigs: medium size with medium internode length; current season's brown, green and red; older growth, brown and gray.
Productivity: heavy bearer, sets fruit regularly.

LEAVES

Shape: lanceolate; tip accuminate.
Size: as taken from new growth 18 to 24 inches long: 6 to 7½ inches long, 1⅜ to 1¾ inches wide; some with leaflets 2½ to 4 inches long and ½ to ⅞ inches wide; medium thick.
Color: dark green on upper surface; medium green on under surface; light yellowish green viens on the under surface.
Class: Classes 2 and 3 on main leaves. Meader and Blake: Proceedings of the American Society for Horticultural Science, Vol. 37, page 203.
Margin: crenate.
Petiole: generally about ⅜ inch long.
Glands: reniform.

FLOWERS

Buds: medium in size, free, plump, pubescent.
Blooms: medium to small in size, pink.
Date of bloom: early, about with Fiesta (U.S. P.P. 1,099).
Pollen: abundant.

FRUIT (described at maturity)

Season of ripening: about with Merrill Halloween I (U.S. P.P. 1,473), which in the breeding area of the instant peach is late September and early October.
Size and shape: variable; generally large and globose except at stem end which is slightly retuse; 2¾ to 3 inches in axial diameter, 2¾ to 3¼ inches transverse in the suture plane, 3 to 3¼ inches at right angle to suture plane (cheek to cheek).
Suture: slightly depressed, with slight roughness on most, extending from base beyond but discontinuous at apex, and with slight depression beyond pistil point.
Dorsal surface: rounded.
Cavity: flaring moderately, elongated in suture plane and showing on both sides; depth ⅜ to ½ inch, breadth ⅞ to 1⅛ inches; marking same as skin surface and showing red when exposed to sun.
Base: retuse.
Apex: mucronate.
Stem: ⅜ to ½ inch in length, longer than on most peaches; diameter ⅛ inch; strongly attached to peach and twig.
Flesh: half way between skin and stone, Chrome Lemon yellow 9–K–2; nearer skin, lighter yellow 9–D–1; near stone, Salvia 3–L–6.
Amygdelin: moderate.
Juice: rich.
Texture: meaty.
Fibers: moderate, fine.
Ripens: evenly.
Flavor: delicate.
Aroma: distinct.
Firmness: firm throughout.
Eating quality: good.

SKIN

Thickness: medium.
Texture: medium tender.
Flavor: sweet.
Color: under color light yellow, 9–L–5 to Florida Gold 10–L–8, with blush and stripes orange-vermilion 2–G–12 to cherry red 2–L–12.
Pubescence: scant.

STONE

Color: light brown, 12–G–8 to Raw Umber 15–A–12.
Tenacity: completely free except adheres to flesh slightly on ventral edge on some fruit when slightly immature.
Fibers: few, short, accuminate.

Size: 1⅜ to 1¾ inches in length, 1 3/16 to 1 5/16 in width, ¾ to ⅞ in thickness. Larger when stone is naturally split.

Form: obovate, apex accuminate; base, oblique, few straight; hilum, oval; sides, equal and unequal.

Surface: irregularly furrowed toward ventral edge and toward apex.

Pitted: irregularly pitted toward base and dorsal edge; pits circular and elongated.

Ventral edge: thick with thin grooves.

Dorsal edge: narrow with one deep groove, narrowing toward apex.

Tendency to split: some, but split does not usually extend to flesh.

USE

Markets: nearby and distant.

Eating quality: meaty, good, not dry.

Shipping quality: good.

Having thus described and illustrated my new variety of peach tree, what is claimed is:

1. A new and distinct variety of peach tree substantially as illustrated and described and being particularly characterized by a moderately vigorous tree of medium size, bearing heavily and regularly a large and firm fruit that ripens very late and has a bright red blush and mottled and striped skin, a comparatively long stem which remains firmly attached to the fruit and twig and results in but little stem crease and natural drop as the fruit matures, and which most resembles and ripens about the same time as Merrill Halloween I (U.S. P.P. 1,473), but is an improvement thereon in being a smaller tree, more highly colored fruit and with a longer stem which remains firmly attached to the fruit and stem.

No references cited.

ROBERT E. BAGWILL, Primary Examiner